US010557111B2

(12) United States Patent
Akai et al.

(10) Patent No.: US 10,557,111 B2
(45) **Date of Patent: *Feb. 11, 2020**

(54) CELL CULTURE VESSEL

(71) Applicant: DAI NIPPON PRINTING CO., LTD., Shinjuku-ku, Tokyo (JP)

(72) Inventors: Tomonori Akai, Tokyo (JP); Masanori Kagota, Tokyo (JP); Takuma Baba, Tokyo (JP)

(73) Assignee: DAI NIPPON PRINTING CO., LTD., Tokyo (JP)

(*) Notice: Subject to any disclaimer, the term of this patent is extended or adjusted under 35 U.S.C. 154(b) by 394 days.

This patent is subject to a terminal disclaimer.

(21) Appl. No.: 14/917,799

(22) PCT Filed: Aug. 21, 2014

(86) PCT No.: PCT/JP2014/071879
§ 371 (c)(1),
(2) Date: Mar. 9, 2016

(87) PCT Pub. No.: WO2015/037407
PCT Pub. Date: Mar. 19, 2015

(65) Prior Publication Data

US 2016/0222335 A1 Aug. 4, 2016

(30) Foreign Application Priority Data

Sep. 11, 2013 (JP) ................................ 2013-188205
Feb. 17, 2014 (JP) ................................ 2014-027771

(51) Int. Cl.
*C12M 1/32* (2006.01)
*C12M 3/00* (2006.01)
(Continued)

(52) U.S. Cl.
CPC ............ *C12M 23/12* (2013.01); *C12M 21/06* (2013.01); *C12M 25/06* (2013.01); *C12M 41/36* (2013.01)

(58) Field of Classification Search
CPC ...................................................... C12M 23/12
(Continued)

(56) References Cited

U.S. PATENT DOCUMENTS 5,749,730 A * 5/1998 Johnsen ............... A61C 19/005 433/163
2004/0058296 A1* 3/2004 Schenck ............... A61C 3/005 433/49

(Continued)

FOREIGN PATENT DOCUMENTS

EP 1691196 A1 8/2006
JP 2006-129713 A 5/2006

(Continued)

OTHER PUBLICATIONS

Schultz et al., "Antibody-based techniques to distinguish proteins and identify sturgeon glue in works of art," 2011, Proceedings of Adhesives and Consolidants for Conservation (Year: 2011).*

(Continued)

*Primary Examiner* — Kevin Joyner
*Assistant Examiner* — Holly M Mull
(74) *Attorney, Agent, or Firm* — Oliff PLC

(57) ABSTRACT

The object of the present invention is to provide a cell culture vessel having a plurality of microwells, which allows to identify the position of a microwell by observing it under a microscope without moving a viewing position, which has identifiers to be easily disposed to the microwells. The present invention is directed to a cell culture vessel comprising a bottom and a sidewall, in which the bottom has a cell containing section in which a plurality of microwells for (Continued)

containing cells are disposed, identifiers are disposed in the vicinities of the plurality of microwells so as to make pairs in individual microwells, and the relative position of each of the identifiers to a partner microwell varies in every pair.

18 Claims, 16 Drawing Sheets

(51) Int. Cl.
*C12M 1/34* (2006.01)
*C12M 1/12* (2006.01)

(58) Field of Classification Search
USPC .................................................... 435/289.1
See application file for complete search history.

(56) References Cited

U.S. PATENT DOCUMENTS

2006/0115315 A1* 6/2006 Discko, Jr. ............... A61C 5/60 401/129
2006/0228722 A1* 10/2006 Kim ...................... B01L 3/5085 435/6.11
2010/0221768 A1 9/2010 Akai et al.
2014/0030755 A1* 1/2014 Allender ............... B01L 3/5085 435/29

FOREIGN PATENT DOCUMENTS

JP 2006-280298 A 10/2006
JP 2009543048 A 12/2009
JP 2010-200748 A 9/2010
JP 4724854 B2 4/2011
JP 201260903 A 3/2012
WO 2008002142 A1 1/2008

OTHER PUBLICATIONS

International Search Report for International Application No. PCT/JP2014/071879 (dated Nov. 25, 2014 (3 Pages).
Japanese Office Action for Japanese Application No. 2014-027771 dated Nov. 17, 2015.(4 Pages).
"Micro-Insert 4 Well", IBIDI, 2011, XP002768352, 3 pages.
Supplementary European Search Report for Corresponding European Application No. EP14843661.1 (dated Apr. 3, 2017) (4 Pages).

* cited by examiner

CELL CULTURE VESSEL

CROSS-REFERENCE TO RELATED APPLICATIONS

This application is a 371 of PCT/JP2014/071879, filed Aug. 21, 2014, which claims the benefit of Japanese Patent Application Nos. 2013-188205, filed Sep. 11, 2013 and 2014-027771, filed Feb. 17, 2014.

TECHNICAL FIELD

The present invention relates to a cell culture vessel for culturing cells such as fertilized eggs requiring individual management.

BACKGROUND ART

Sperms and eggs are fertilized in vitro in a culture system to prepare fertilized eggs (zygotes) and the fertilized eggs can be further cultured until they are developed into cleavage, morula and blastocyst stages and hatched from zona pellucida into the hatched blastocyst stage. A technique of implanting a fertilized egg in the cleavage to blastocyst stage into the uterus to obtain an offspring, i.e., assisted reproductive technology (ART) has been established not only in the field of livestock but also in medical treatment for human infertility.

However, the rate of successful pregnancy by in vitro fertilization is not always high. For example, in human, the rate of successful pregnancy still remains at about 25 to 35%. As a cause of this, it is pointed out that the probability of obtaining a good fertilized egg suitable for implantation to the uterus by culture is not high. The fertilized eggs obtained by culture are individually subjected to microscopic observation by an expert to determine whether the fertilized eggs of good quality are suitable for uterus implantation.

In the in vitro fertilization, a micro-drop method, in which a drop of culture medium is prepared in a vessel, and a fertilized egg is introduced in the drop and subjected to in vitro culture, is frequently used. In the micro-drop method known in the art, a petri dish of 30 to 60 mm in diameter having a uniform flat bottom surface is used as a cell culture vessel. On the bottom surface of the petri dish, a plurality of drops of culture medium are prepared at intervals and cells are cultured in the drops. Such a cell culture method has been used.

When a drop is prepared in a petri dish conventionally used, the position of a fertilized egg changes depending upon the cellular motion of the fertilized egg itself and convection within the drop. Thus, it is difficult to identify the fertilized egg cultured in the drop and monitored. Because of the problem, it has been desired to develop means for controlling the position of a fertilized egg.

To more efficiently obtain the culture effect of a fertilized egg, it is preferable to use interaction of fertilized eggs to each other (paracrine effect). For controlling the position of a fertilized egg while using the effect, a system in which microwells having the same size as that of the fertilized egg are formed in the bottom surface of a petri dish and drop of culture medium is added so as to cover the microwells, and then fertilized eggs are disposed in microwells filled with the culture medium and cultured is known. Owing to the system, a plurality of fertilized eggs can be cultured in a small amount of culture medium while successfully controlling the positions of a plurality of fertilized eggs so as to enable monitoring of individual eggs, and the paracrine effect can be used.

To distinguish individual fertilized eggs, individual microwells must be distinguished. Since microwells are observed by a microscope, a lot of information must be estimated only from a microscope field; however, at a high magnification, which microwell is observed cannot be determined. To distinguish microwells, numerical or literal information tags are disposed to the outermost periphery of a microwell array. In this way, it is known that the microwells are distinguished with the help of a matrix system. However, this method had a problem in operability because when observation is made under a microscope at high magnification, it is necessary to read identification information by shifting the viewing position far away from the microwell. In addition, when cells are photographed by a microscope, the identification information of the microwell is not present in the photograph and thus the information must be manually provided to the photo data. Because of this, the operation was intricate and there was a risk of mistakenly associating information by the operator.

CITATION LIST

Patent Literature

Patent Literature 1: JP Patent No. 4724854

SUMMARY OF INVENTION

Technical Problem

The object of the present invention is to provide a cell culture vessel having a plurality of microwells, which allows identification of the position of a microwell by observing it under a microscope without moving a viewing position, and having identifiers to be easily disposed to the microwells.

Solution to Problem

The present inventors have found that the aforementioned problems can be solved by attaching, in a cell culture vessel having a plurality of microwells, identifiers to individual microwells so as to make pairs and arranging microwells and identifiers such that the relative positions of identifiers to the partner microwells mutually vary or such that length or orientation of linear identifiers mutually varies in every partner microwell.

More specifically, the present invention includes the following inventions.

(1) A cell culture vessel comprising a bottom and a sidewall, in which the bottom has a cell containing section in which a plurality of microwells for containing cells are disposed, identifiers are disposed in the vicinities of the plurality of microwells so as to make pairs in individual microwells, and the relative position of each of the identifiers to a partner microwell varies in every pair.

(2) The cell culture vessel according to (1), in which, in the top view, each of the identifiers has a smaller area than the opening of each of the microwells.

(3) The cell culture vessel according to (1) or (2), in which the identifiers have a dot or linear shape.

(4) The cell culture vessel according to any one of (1) to (3), in which the plurality of identifiers, which are to be disposed to the plurality of microwells whose centroids are positioned on a same axis to make pairs therewith, are disposed on a same axis.

(5) The cell culture vessel according to any one of (1) to (4), in which all of the identifiers are disposed to right sides alone, left sides alone, upper sides alone or lower sides alone with respect to the center of each of the microwells.

(6) The cell culture vessel according to any one of (1) to (5), further comprising a second identifier for specifying the orientation of the cell culture vessel, in which, in the top view, the second identifier has a larger area than the opening of each of the microwells, so as to be visually confirmed.

(7) The cell culture vessel according to any one of (1) to (6), in which a microwell to which the plurality of identifiers are disposed to make pairs is present.

(8) The cell culture vessel according to (7), in which the plurality of identifiers disposed to the partner microwell to make pairs are different in shape.

(9) The cell culture vessel according to any one of (1) to (8), in which a microwell having no identifiers disposed thereto is present.

(10) The cell culture vessel according to any one of (1) to (9), in which the vicinity of the microwell is divided into a plurality of regions and the presence or absence of the identifier in the regions varies in every microwell-identifier pair.

(11) A cell culture vessel comprising a bottom and a sidewall, in which the bottom has a cell containing section in which a plurality of microwells for containing cells are disposed, identifiers having a linear shape are disposed in the vicinity of the plurality of microwells so as to make pairs, and the identifiers having a linear shape mutually vary in length or orientation in every identifier-microwell pair.

Advantageous Effects of Invention

Owing to the present invention, in a cell culture vessel having a plurality of microwells, the positions of individual microwells can be easily identified by microscopic observation.

DESCRIPTION OF EMBODIMENTS

Now, the present invention will be described.

Figure 1:
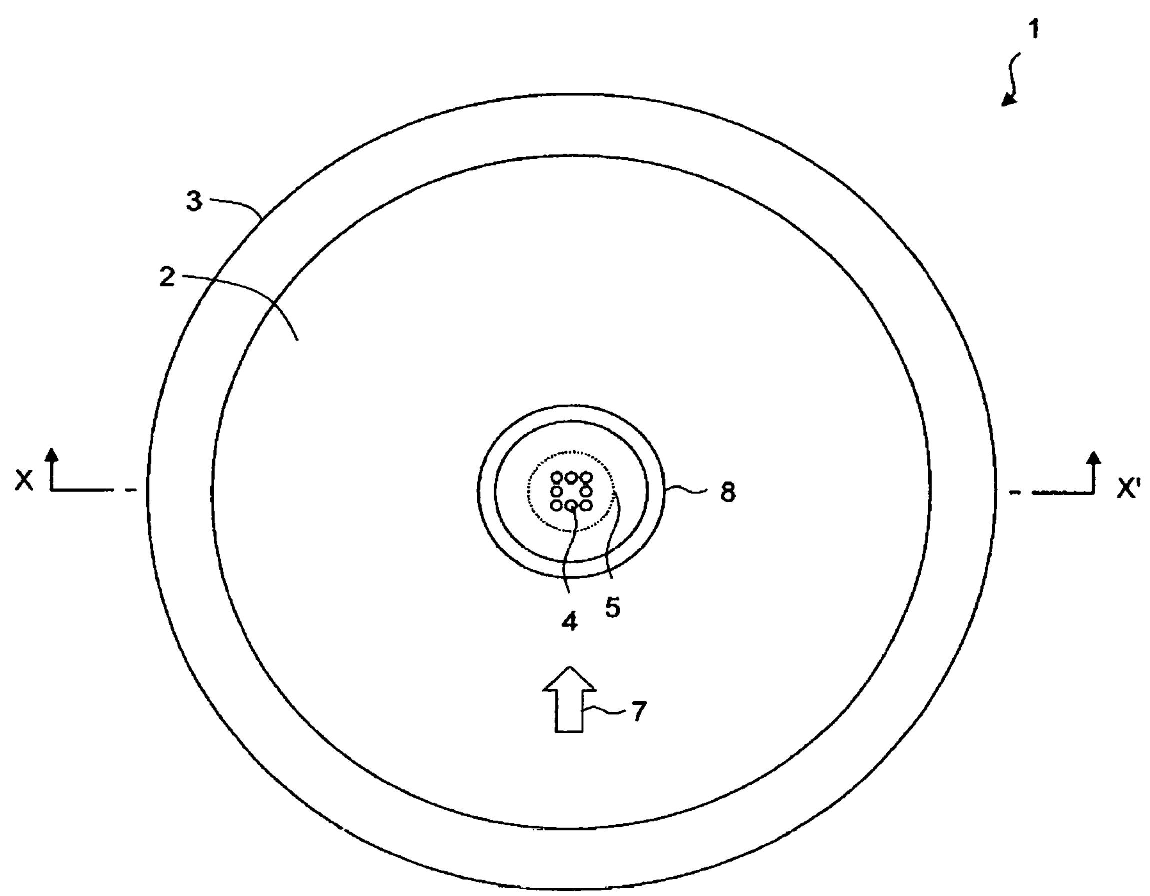
FIG. 1 is a schematic view showing the top view of an embodiment of the cell culture vessel according to the present invention.
Figure 2:
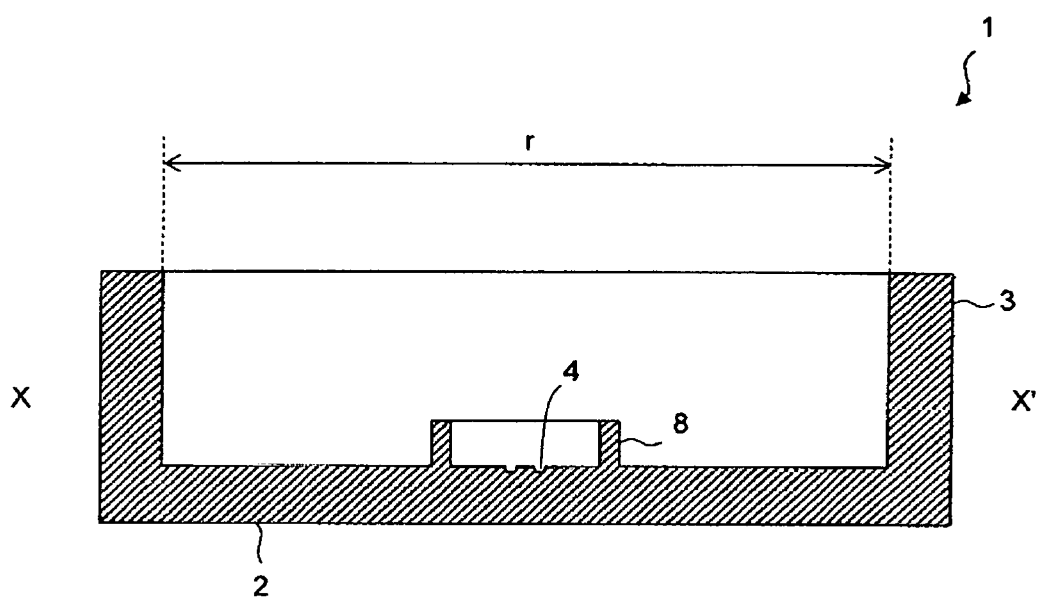
FIG. 2 is a schematic view showing a vertical cross-sectional view of an embodiment of the cell culture vessel according to the present invention.
Figure 3:
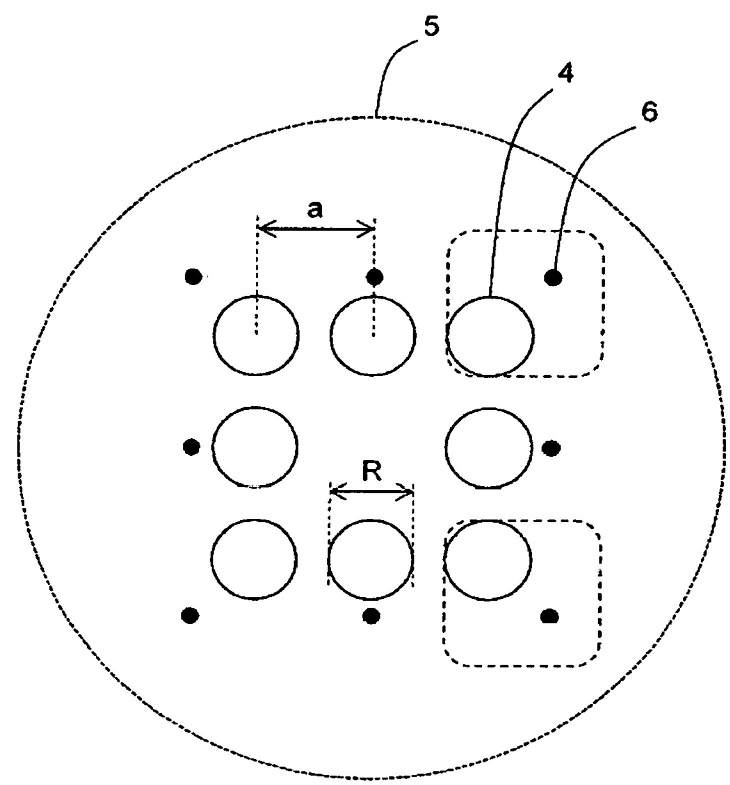
FIG. 3 is a schematic view showing an enlarged top view of a cell containing section of an embodiment of the cell culture vessel according to the present invention.

As shown, for example, in FIGS. 1 to 3, a cell culture vessel 1 according to an embodiment of the present invention has a bottom 2 and a sidewall 3, and the bottom has a cell containing section 5 having a plurality of microwells 4 for containing a cell disposed. In the vicinities of these microcells, identifiers 6 are respectively disposed so as to make pairs with the microcells. The relative position of an identifier to a microwell to make a pair varies in every identifier-microwell pair. Owing to the difference in relative position of an identifier to a microwell in every identifier-microwell pair, if a single identifier-microwell pair is just observed, the position of the microwell in the plurality of microwells can be identified. Since the identifier is disposed in the vicinity of each microwell, it is not necessary to move a viewing position far from the microwell when observation is made at high magnification and quick observation can be made. In addition, when a cell is photographed at high magnification, an identifier can be photographed together with a microwell. Because of this, it is not necessary to manually attach information to the photo data. As a result, intricate work and a risk of mistakenly associating information by the operator can be avoided.

The microwells preferably form recessed parts suitable for individually containing cells such as fertilized eggs and the size of the microwells is very small. The present invention is characterized by attaching a minute identifier to every such a minute microwell. To be more specific, the area of the opening of each microwell in a top view of the cell culture vessel is preferably 3 $mm^2$ or less, more preferably 1 $mm^2$ or less, and further preferably 0.5 $mm^2$ or less; and preferably 0.03 $mm^2$ or more.

The microwell forms a recessed part having a wall surface and an opening. The recessed part may be a recession directly formed on the bottom of a cell culture vessel or a recessed part formed by a member projecting from the bottom. Accordingly, the area of the opening of a microwell in the top view is, in other words, the area of a figure formed by the outer periphery of the opening of a microwell. The figure formed by the outer periphery of the opening of a microwell, which is not particularly limited, may be a polygon such as a triangle and a square or a circle (including a circle, a substantial circle, an ellipse and a substantial ellipse); however, a circle is preferable.

If the outer periphery of the opening of a microwell is a circle, the opening width is equal to the diameter of the circle (indicated by R in FIG. 3). The diameter is larger than the maximum size of the cell to be cultured. In culturing fertilized eggs by the cell culture vessel of the present invention, since they are desirably cultured up to the blastocyst stage, the diameter of the circular opening is desirably larger than the maximum size of a cell in the blastocyst stage. Furthermore, when the outer periphery of the opening of a microwell forms a circle, the opening width is smaller than the pitch between the microwells. Accordingly, the opening width of the opening (if the outer periphery of the opening of a microwell is circle, the diameter of the circle is meant) of a microwell is preferably 0.1 mm or more, more preferably 0.15 mm or more and further preferably 0.2 mm or more; and preferably below 0.6 mm and further preferably below 0.4 mm. Moreover, the opening width of the opening of a microwell can also be defined to be X+m (X herein represents the maximum diameter of a cell). Herein, m herein is preferably 0.01 mm or more and further preferably 0.02 mm or more.

In the bottom of the cell culture vessel of the present invention, preferably 4 or more and further preferably 8 or more of microwells (for example, 10 or more); and preferably 50 or less, and more preferably 30 or less of microwells are disposed. Accordingly, a plurality of cells such as fertilized eggs can be disposed one by one to a microwell and cultured. Since a plurality of cells such as fertilized eggs are disposed close to each other in the same system and cultured in this state, a good paracrine effect and an autocrine effect can be expected. The culture in the same system means culture performed in flowable (communicable) culture medium without being isolated, preferably in a drop of the same culture medium.

The pitch between microwells is preferably 1 mm or less, more preferably 0.8 mm or less and further preferably 0.6 mm or less. As the observation device, the device equipped with a ½-inch CCD element and an objective lens with magnifications of ×4, ×10, and ×20, is commonly used. The observable field with such an observation device, when an objective lens with a magnification of ×4 is selected, is about 1.6 mm×1.2 mm, and it is preferable to design so that at least four microwells are included in the observation field.

The pitch between the microwells is a distance between the centers of the microwells adjacent to each other (for example, indicated by a in FIG. 3). The center of the microwell is the centroid of a figure formed by the outer periphery of the opening of the microwell and, when the outer periphery is circle, refers to the center of the circle. The pitch between microwells typically means an average pitch, and the average pitch for a certain microwell means the average value calculated from the pitches of all the microwells adjacent to the certain one. The pitch between microwells is larger than the size of the outer periphery of the opening of a microwell. If the outer periphery of the opening forms a circle, the size of the outer periphery of the opening of a microwell means its diameter. If the outer periphery does not form a circle, it means a minimum diameter of the figure formed by the outer periphery of the opening of a microwell. A plurality of microwells adjacent to each other are preferably disposed in the form of a tetragonal lattice or close-packing form. For example, the case where 25 microwells are disposed in the form of a 5×5 square lattice can be mentioned. Owing to the arrangement of the tetragonal lattice or close-packing form, the positions of individual microwells in the bottom of a culture vessel can be further easily specified in combination with an identifier and easily applied to automation processing.

The arrangement of the plurality of microwells may be acceptable if some of the microwells are missing from a tetragonal lattice or close-packing form. For example, the case where a cell containing section is configured by disposing 8 or more microwells at equal intervals on the sides and vertexes of a parallelogram, can be mentioned. Examples of the parallelogram include a square, a rectangular, a rhombic and other types of parallelograms. Disposing microwells at equal intervals on the sides and vertexes of a parallelogram means that the centroids of the figures formed by the outer periphery of microwells are disposed on the sides and the vertexes of the parallelogram. For example, in the embodiment shown in FIG. 3, 8 microwells are disposed at 4 vertexes and at 4 middle points of the sides, one by one.

The position of an identifier to be disposed to a partner microwell to make a pair may be inside or outside the microwell; however, the position is preferably outside the microwell.

This is because if an identifier is provided within a microwell, there is a possibility of inhibiting observation of a fertilized egg and affecting culturability of a fertilized egg. The identifiers are preferably disposed in the spaces between the plurality of microwells disposed as mentioned above. The identifier is small enough to be disposed in the space. The size of the identifier is preferably smaller than the size of a microwell. Accordingly, in the top view of a cell culture vessel, the size of the identifier is preferably small enough to fall within the figure formed by the opening of a microwell. More specifically, the area of the identifier in the top view of a cell culture vessel is 30,000 $\mu m^2$ or less, preferably 15,000 $\mu m^2$ or less, more preferably 8,000 $\mu m^2$ or less; and preferably 100 $\mu m^2$ or more.

The identifier is disposed to a site in close vicinity of a partner microwell in order to clearly indicate which microwell the identifier makes a pair with. Accordingly, each identifier is preferably disposed such that distance from a partner microwell is the shortest of the distances from all microwells. The distance between an identifier and a microwell is defined as the distance between the centroid of the figure formed by the opening of the microwell and the centroid of the figure formed by an identifier. Accordingly, the distance between an identifier and a microwell is preferably larger than ½ of opening width of the microwell and smaller than the pitch between microwells. To describe more specifically, the distance between an identifier and a microwell is preferably 500 μm or less, more preferably 400 μm or less and further preferably 300 μm or less.

The identifiers are preferably disposed to all microwells within the cell containing section; however the present invention includes the case where several microwells having no identifiers disposed thereto are present. (for example, 10% or less of the all microwells contained in the cell containing section). This is because even if microwells containing no cell, which are not observation targets, are present, it is not necessary to attach an identifier to such microwells. A single identifier is preferably disposed to a partner microwell; however, two or more identifiers may be disposed. The amount of information can be increased by varying the number of identifiers to be disposed to a partner microwell to make pairs.

The shape of an identifier, more specifically, the shape of the figure that an identifier forms is not particularly limited. Examples of the figure include letters, numerical characters, graphic shapes such as a polygon, an arrow, a line (bar) and a dot, bar codes such as a QR code and combinations thereof. Since an identifier is disposed in the vicinity of a minute microwell suitable for containing a single cell such as a fertilized egg and the identifier is preferably smaller than the size of the microwell, the identifier preferably has a simple shape that can be easily molded. This is because the cell culture vessel is often manufactured by injection molding and thus it is difficult to form a complicated shape in a small size. Even if the shape of the identifier is simple, in other words, even if the amount of information that the identifier itself has is not large, since the relative position of the identifier to a microwell is added as information, the position of each microwell can be identified. If the shape of the identifier is complicated, there is a risk of reducing the production yield of a cell culture vessel; however, since the identifier has a simple shape herein, reduction in yield can be avoided and manufacturing cost can be reduced. In the case where two or more of identifiers are disposed to every microwell, the shape of the plurality of identifiers to be disposed to a single microwell may be the same or different. The amount of information can be increased by attaching identifiers different in shape. The identifiers different in shape means that at least one identifier different in shape is present among the plurality of identifiers.

The identifier preferably has a dot or linear (bar) shape. A dot identifier and a linear identifier may be used in combination per single cell culture vessel and single cell containing section. The amount of information can be increased by combination use of them. The amount of information that an identifier itself has can be increased by changing the length of the linear identifier. Furthermore, the amount of information that an identifier itself has can be increased by changing the orientation of the identifier. The "orientation" herein means a rotation angle, which differs from angle α (described later). To describe more specifically, in the embodiment shown in FIG. 4, if the dot is replaced by a line (bar), the rotation angle (autorotation) of the line (on the position of the dot) relative to the straight line X, in other words, the angle formed between straight line X and the identifier, is referred to as the rotation (autorotation) angle. The amount of information given by the orientation and angle α can be used for specifying the orientation of a culture vessel. Accordingly, if the linear identifiers, which are mutually different in length or orientation, are disposed in every microwell, even if the relative position of an identifier to a partner microwell is not changed, the position of a specific one of microwells can be specified among the plurality of microwells. The amount of information can be increased by using orientation and length in combination.

Figure 4:
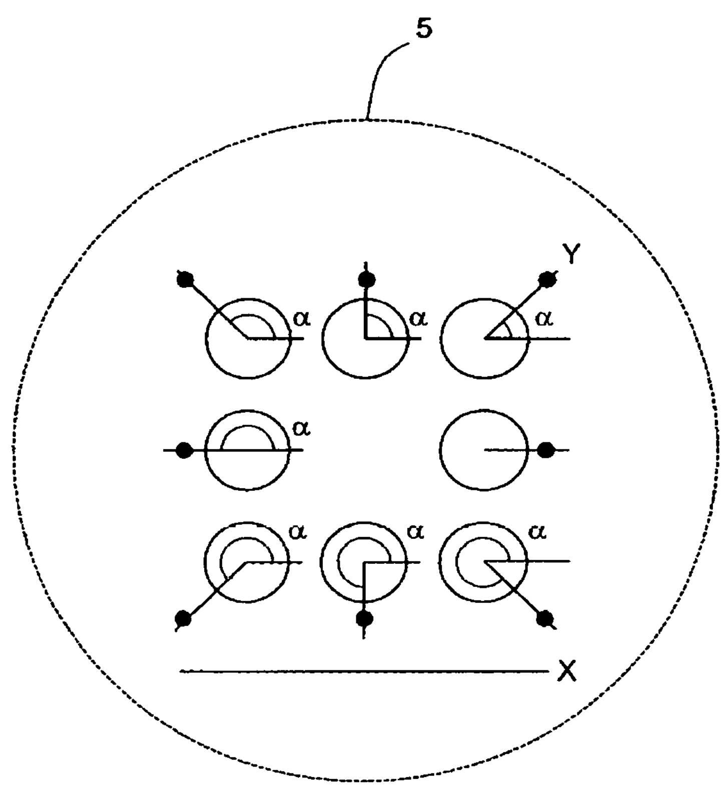
FIG. 4 is a schematic view showing an enlarged top view of a cell containing section of an embodiment of the cell culture vessel according to the present invention.

Examples of the case where the relative position of an identifier to its partner microwell varies in every identifier-microwell pair include a case where the distance between an identifier and its partner microwell varies in every pair and a case where the angle of the identifier to its partner microwell varies. The distance between an identifier and a microwell is the same as defined above. The angle α of the identifier to its partner microwell can be defined as follows. For example, in the embodiments shown in FIGS. 1 to 3, when straight line X is drawn at the bottom of a cell culture vessel in the top view, angle α can be defined as the angle formed between the straight line parallel to straight line X and straight line Y connecting the centroid of a microwell and the centroid of an identifier (FIG. 4). The centroid of a microwell means a centroid of the figure formed by the outer periphery of the opening of the microwell; whereas, the centroid of an identifier means a centroid of the figure formed by the identifier. If every identifier is disposed at a different angle α with its partner microwell, the position of a specific microwell can be identified among the plurality of microwells. The amount of information can be increased by using distance and angle in combination.

If the vicinity of a microwell is divided into a plurality of regions and the presence or absence of an identifier in individual regions is varied in every identifier-microwell pair, the relative position of an identifier to a microwell can be varied in every pair. For example, in the embodiment shown in FIG. 13, the vicinity of each of the microwells is divided into three regions. The presence or absence of an identifier in individual regions is different in every identifier-microwell pair. In microwell C, an identifier is present only in the top region and absent in the other regions. In contrast, in microwell B, an identifier is present in all regions. Likewise, by changing the presence or absence of an identifier in every region, the position of a specific microwell can be identified among the plurality of microwells.

The presence or absence of an identifier in each region can be checked based on the presence or absence of the centroid of the identifier in each region. Accordingly, in the case where the plurality of identifiers are disposed to every microwell to make pairs, the identifiers may be overlapped as long as the positions of the centroids of the individual identifiers can be specified. For example, in the case of dividing the vicinity into three regions, $2^3$ identifier arrangement patterns are conceivable and the positions of at least 8 microwells can be specified. A microwell with the regions in which no identifiers are present may be present, like microwell G of FIG. 13. Likewise, the position of a single microwell can be identified.

However, for the purpose of specifying a microwell, the number of microwells with no identifier disposed is limited to only one. The border lines between the regions may be imaginary and need not actually exist.

The number of regions to be divided, which is not particularly limited, can be preferably 3 to 10 and more preferably 4 to 6. The dividing method is not particularly limited. For the reason that readout is easy, the region is preferably divided into a lattice form consisting of rows and lines. The number of rows is preferably 1 to 3 and more preferably 1 to 2. The number of lines is preferably 1 to 6 and more preferably 3 to 5. When identifiers are disposed on the left or right side of a microwell, if the numbers of rows and lines fall within the above ranges, the identifiers can be disposed as close to the position of the microwell as possible. When identifiers are disposed above or below a microwell, if the above ranges in number of lines and rows are interchanged with each other, the identifiers can be disposed as close to the position of the microwell as possible.

Figure 14:
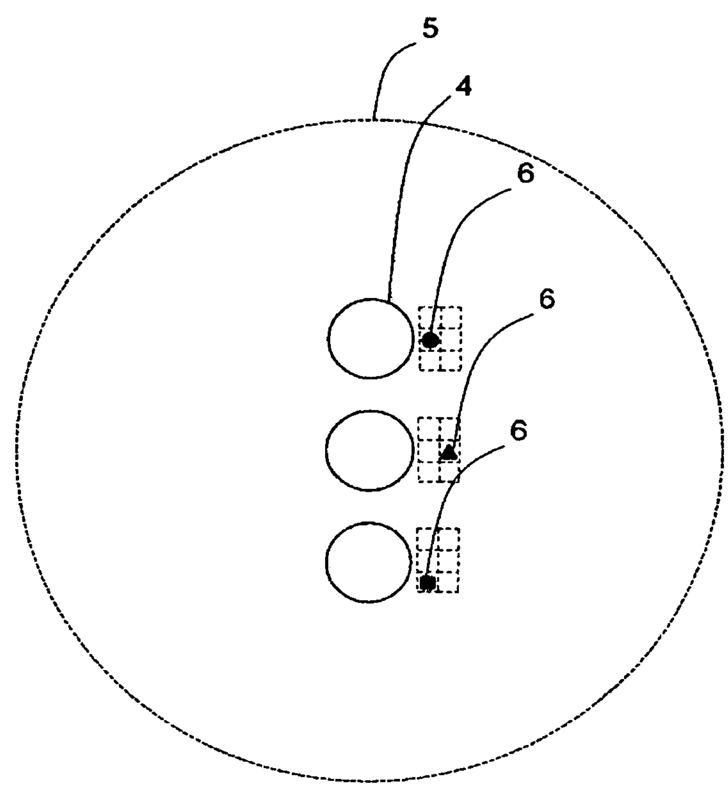
FIG. 14 is a schematic view showing an enlarged top view of a cell containing section of an embodiment of the cell culture vessel according to the present invention.

For example, FIG. 14 shows an embodiment in which the vicinity of a microwell is divided into a lattice form constituted of two rows and three lines. In the embodiment of FIG. 14, identifiers are different in shape. Due to this, the amount of information can be further increased.

When the plurality of identifiers are disposed to every microwell to make pairs, the identifiers are disposed such that the relative position of at least one identifier to its partner microwell differs in every identifier-microwell pair. More specifically, when a plurality of microwells are compared, as long as at least one identifier whose relative position to its partner microwell differs may be present, identifiers whose relative positions (to their partner microwell) are identical may be present. For example, in the embodiment shown in FIG. 13, when two identifiers disposed to microwell A are compared to two identifiers disposed to microwell D, identifier a and identifier a' are disposed in the same position relative to the respective microwells; whereas identifier b and identifier c are disposed in different positions relative to the respective microwells. Thus, the positions of microwells can be identified. The centroids of the plurality of identifiers are preferably disposed not on the circumference but on the straight line, like microwells of e.g., A, B, D and F in FIG. 13. This is because, as described below, whether a cell culture vessel itself is rotated or not can be determined even if single microwell-identifier pairs are photographed one by one at high magnification.

Figure 5:
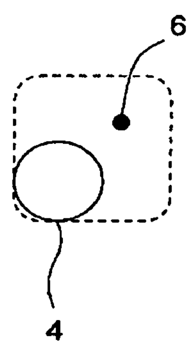
FIG. 5 shows a conceptual diagram of a microscope photograph of a microwell-identifier pair.
Figure 6:
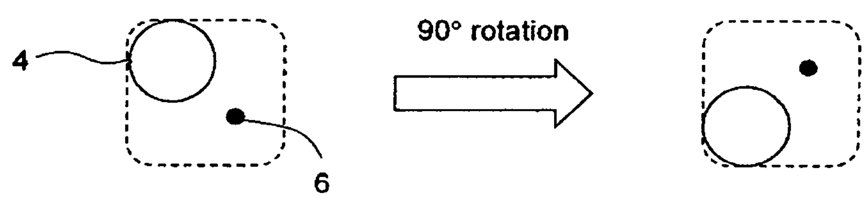
FIG. 6 shows a conceptual diagram of a microscope photograph of a microwell-identifier pair.
Figure 7:
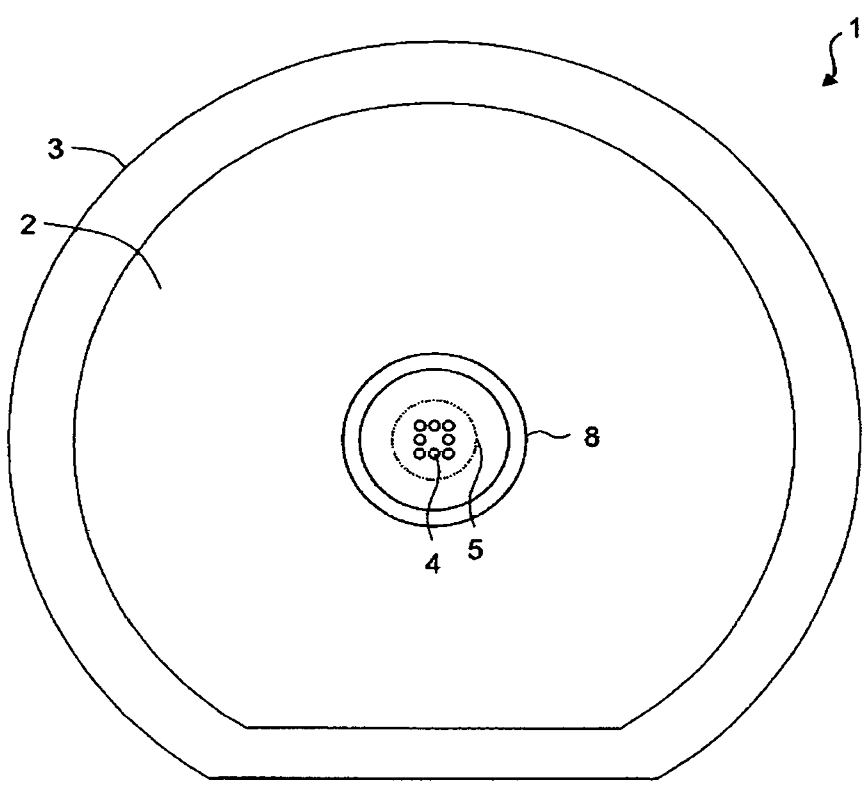
FIG. 7 is a schematic view showing the top view of an embodiment of the cell culture vessel according to the present invention.

In a plurality of microwell-identifier pairs are photographed by repeating a process of photographing a single microwell-identifier pair at high magnification, multiple times, it is necessary to always keep a constant orientation of the cell culture vessel when photographed. This is because, if not, the inclination angle of the cell culture vessel itself comes to be added to the above angle α, with the result that even though relative positions of identifiers differ in a cell culture vessel, they cannot be often distinguished in the photograph. For example, the photograph (FIG. 5) of a microwell 4-identifier 6 pair, which is disposed at the upper right vertex in the enlarged view of a cell containing section 5 shown in FIG. 3, cannot be distinguished from the photograph (FIG. 6) of a microwell 4-identifier 6 pair, which is a photograph of a microwell 4-identifier 6 pair disposed at the lower right vertex in FIG. 3, taken after the cell culture vessel is rotated by 90° in a counterclockwise direction from the state of FIG. 3. In order to always keep a constant orientation of a cell culture vessel when photographed, it is preferable to attach another identifier, i.e., a second identifier, for specifying the orientation of a cell culture vessel. The second identifier, since it is used for photo-taking, is preferably an identifier visually confirmed. Accordingly, in the top view of a cell culture vessel, the area of a second identifier is preferably larger than the area of the opening of a microwell. The second identifier is preferably positioned on the bottom and outside the cell containing section having a plurality of microwells disposed therein (for example, reference symbol 7 in FIG. 1). The second identifier may be disposed to the sidewall of a cell culture vessel. Alternatively, the orientation of a cell culture vessel can be kept always constant by the shape of the cell culture vessel itself. More specifically, if a shape which can specify the orientation of a cell culture vessel, e.g., a circle partly having a missing portion (FIG. 7), is employed as the outer peripheral shape of the sidewall of a cell culture vessel, the orientation of the cell culture vessel when photographed can be kept always constant. The shape of the cell culture vessel herein is not particularly limited as long as it can specify the orientation of the cell culture vessel.

If an identifier is linear, unlike a dot identifier, the identifier has two-dimensional information. Because of this, even if a second identifier is not used, the orientation of a cell culture vessel can be specified to some extent in the photograph of a microwell-identifier pair taken at high magnification. More specifically, even if linear identifiers all facing in the same direction are used as viewed from the top of a cell culture vessel, the orientation of the cell culture vessel can be specified to some extent based on the direction of the line (bar).

If identifiers are disposed to the right side alone, the left side alone, the upper side alone or the lower side alone of all of the microwells of the cell containing section, the orientation of the cell culture vessel can be specified even in the photograph of a microwell-identifier pair taken at high magnification. Since the position of an identifier is approximately predetermined in every target microwell to some extent, it is easy to determine the shooting position when a fertilized egg is photographed at high magnification. If the identifiers are not placed in the same direction, like e.g., a case where an identifier is placed at the slightly left side from the center and another identifier is placed at the slightly lower side from the center, the researcher must determine a shooting position while looking for the position(s) of the identifier(s) around (360°) the field of vision in every well.

The right, left, upper, and lower sides of a microwell are defined respectively as the four regions obtained by dividing the periphery around the centroid of a microwell by 4. For example, the range specified by an angle α of 45 to 135° shown in FIG. 4 is defined as the upper side. Even if an identifier is disposed only to the upper side of a microwell, the relative position of the identifier to the microwell can be varied within the upper-side range.

Figure 8:
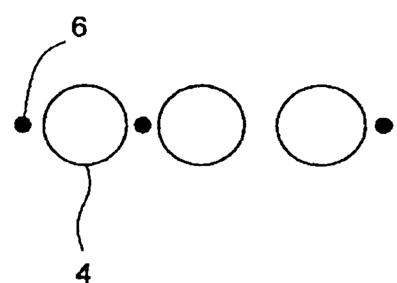
FIG. 8 is a schematic view showing an embodiment in which a plurality of identifiers are disposed on the same axis.
Figure 9:
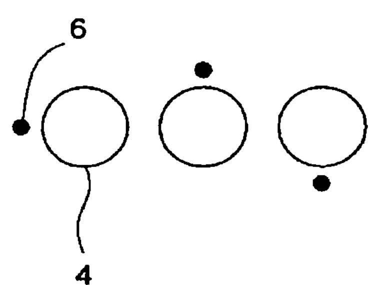
FIG. 9 is a schematic view showing an embodiment in which a plurality of identifiers are not disposed on the same axis.

It is sometimes preferable that the plurality of identifiers to be disposed to the respective plurality of microwells are disposed on the same axis. The plurality of microwells herein are not necessarily referred to all of the microwells within a cell containing section and preferably referred to 2 or more microwells, more preferably 3 or more, further preferably 4 or more microwells whose centroids are disposed on a same axis. If the identifiers to be disposed to the plurality of microwells whose centroids are disposed on a same axis, are disposed on a same axis, even if an observation target, i.e., a microwell, is changed in observation at high magnification, a microwell-identifier pair can be captured by moving the cell culture vessel only along the X axis or Y axis relative to the lens. Because of this, quick observation can be made. In microscopic observation, since the field of vision is horizontally long in general, a plurality of identifiers arranged along the horizontal axis can be observed at a time (FIG. 8). All identifiers can be observed even at higher magnification by aligning the long side of the field of vision of a microscope with the axis direction of identifiers. This is particularly advantageous in the case where e.g., the length of the short-side of the field of vision is just as close as the diameter of a microwell. In contrast, if identifiers are disposed as shown in FIG. 9, the identifier disposed to the lower side of the rightmost microwell may fall outside the field of vision.

Disposing a plurality of identifiers on a same axis is not intended to mean disposing the centroids of identifiers accurately on the same axis and may be more or less deviated from the axis as long as quick observation can be made at high magnification. For example, as shown in FIG. 10, when straight line X' connecting the centroids of the plurality of microwells is drawn and straight line Y' connecting the centroid of an identifier and the centroid of a partner microwell is drawn, it is satisfactory if the angle β between X' and Y' falls within the range of 45° to 135°.

Now, specific embodiments regarding the arrangement of microwells and identifiers will be described below.

In the embodiment shown in FIGS. 1 to 4, 8 microwells are disposed at 4 vertexes of a square and the middle points of 4 sides thereof one by one, constituting a cell containing section. Dot identifiers are disposed one by one in the vicinity of each of the microwells. In this embodiment, since the angles α between the identifiers and microwells mutually differ, if a single microwell-identifier pair is just observed, the position of each microwell can be specified.

Figure 10:
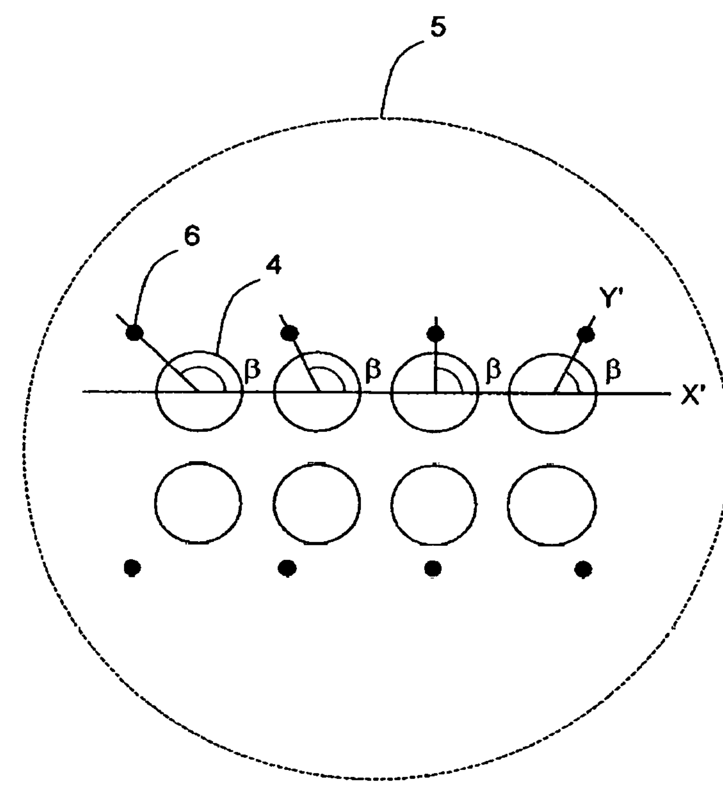
FIG. 10 is a schematic view showing an enlarged top view of a cell containing section of an embodiment of the cell culture vessel according to the present invention.

In the embodiment shown in FIG. 10, a cell containing section is constituted of microwells disposed in the form of a square lattice, which is obtained by disposing 8 microwells at 4 vertexes of a rectangle one by one and at only 2 of the 4 sides two by two at the same intervals. Dot identifiers are disposed one by one in the vicinity of each of the microwells. In this embodiment, since the angles α between the identifiers and microwells mutually differ, if a single microwell-identifier pair is just observed, the position of each microwell can be specified. In addition, 4 identifiers, which are respectively disposed to the upper-stage 4 microwells whose centroids are disposed on a same axis, are disposed on a same axis.

Figure 11:
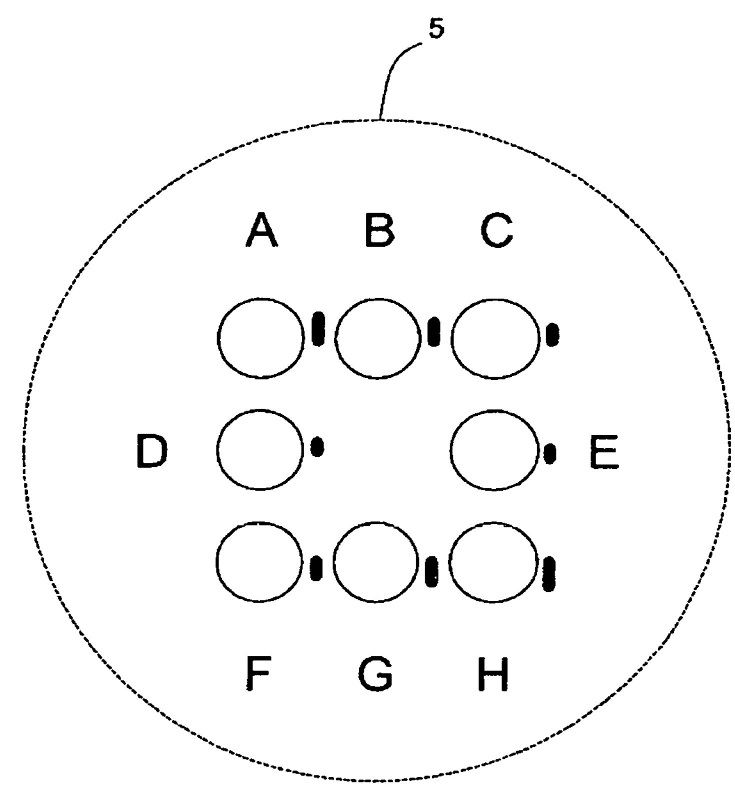
FIG. 11 is a schematic view showing an enlarged top view of a cell containing section of an embodiment of the cell culture vessel according to the present invention.
Figure 12:
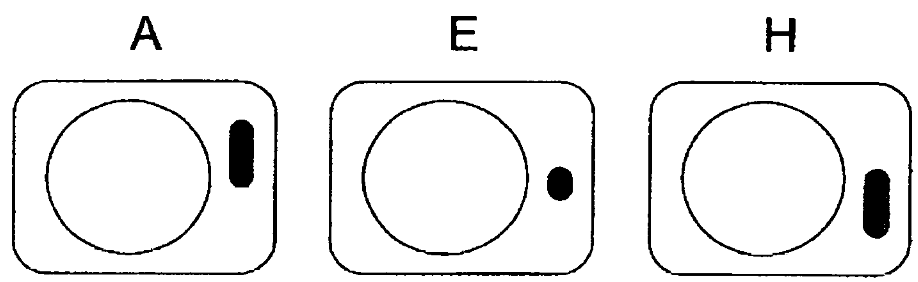
FIG. 12 shows a conceptual diagram of a microscope photograph of a microwell-identifier pair.

In the embodiment shown in FIG. 11, similarly to FIG. 3, a cell containing section is constituted by disposing 8 microwells at 4 vertexes of a square and the middle points of 4 sides thereof one by one. Linear identifiers are disposed one by one in the vicinity of each of the microwells. FIG. 12 shows respective micrographs of microwell-identifier pairs at the positions A, E and H of FIG. 11. In this embodiment, the distance between an identifier and a microwell is almost equal in all the pairs; however, angle α (between an identifier and a microwell) and/or the length of a line (bar) differ from pair to pair. Thus, if a single microwell-identifier pair is just observed, the position of each microwell can be specified. In addition, since the identifiers are all lines disposed in the same direction and disposed to the right side of the microwells, even in a photograph of a microwell-identifier pair taken at high magnification, the orientation of a cell culture vessel at the time of shooting can be specified based on the position and orientation of a line (bar) of the identifier.

Figure 13:
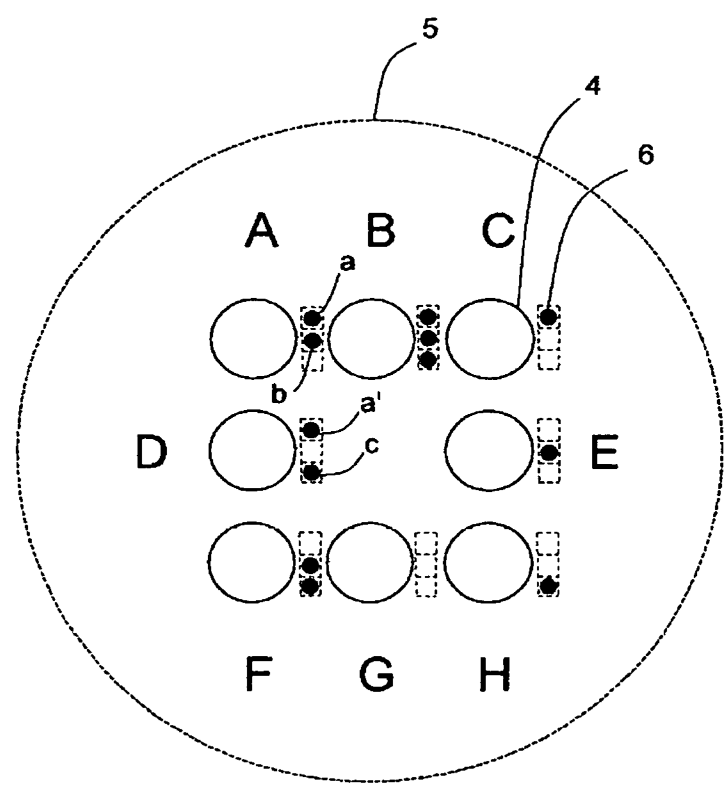
FIG. 13 is a schematic view showing an enlarged top view of a cell containing section of an embodiment of the cell culture vessel according to the present invention.

In the embodiment shown in FIG. 13, similarly to FIG. 3, a cell containing section is constituted by disposing 8 microwells at 4 vertexes of a square and the middle points of 4 sides one by one. One, two or three dot identifiers are disposed as a group to every microwell and the relative position of at least one identifier to a partner microwell differs in every identifier-microwell pair. The vicinity of each microwell is divided into three regions and the presence or absence of an identifier in each region differs in every identifier-microwell pair. Thus, if a single microwell-identifier pair is just observed, the position of each microwell can be specified. Note that, the border lines between the regions in FIG. 13 are imaginary and need not actually exist.

As described above, if the vicinity of each of 8 microwells is divided into three regions and a group of identifiers in which the presence or absence in individual regions differs are disposed, $2^3$ arrangement patterns are conceivable. Thus, microwells can be identified by a minimum number of identifiers. If the number of the regions at which an identifier is disposed is small, the size of an identifier can be increased. This is advantageous in view of identification accuracy and production accuracy.

Figure 15:
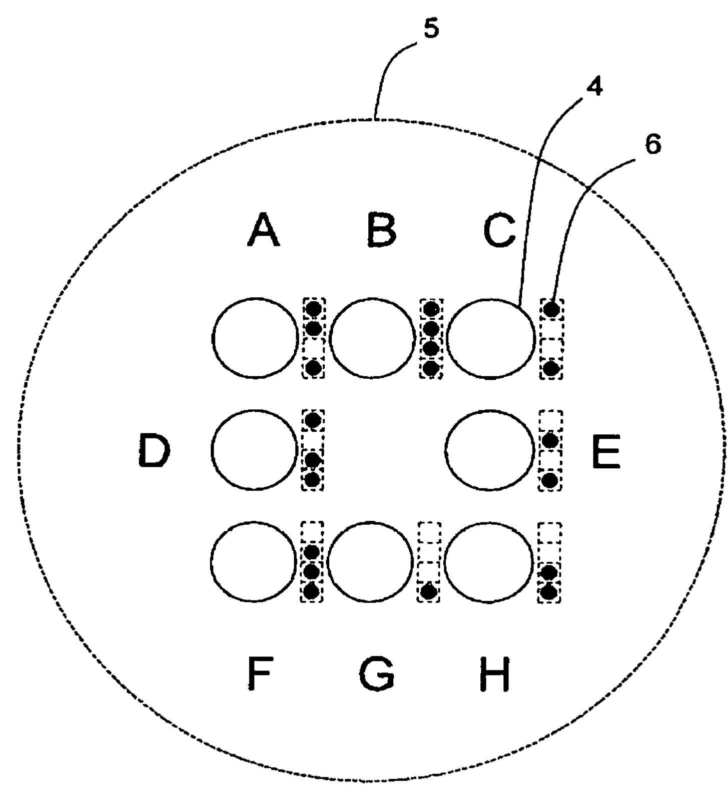
FIG. 15 is a schematic view showing an enlarged top view of a cell containing section of an embodiment of the cell culture vessel according to the present invention.

In contrast, as shown in FIG. 15, the vicinity of each microwell is divided into 4 regions and a group of identifiers may be disposed such that the presence or absence of dot in individual regions mutually differs. In the case of FIG. 13, there is a microwell whose position is identified by the absence of identifier in all regions; however, in the case of FIG. 15 where the vicinity is divided in 4 regions, it is possible to constitute 4 regions such that one identifier is definitely present. If so, it is possible to recognize the inclination at the time of shooting based on the relative position of the 4th-line dot in any microwell. In addition if the operator photographs so as to bring the 4th-line dot into the field of view, it is possible to prevent the operator to choose a wrong shooting range. In the case where the 4th-line dot is used for a specific purpose as mentioned above, the shape of the 4th-line dot alone may be changed.

The cell culture vessel of the present invention has a bottom and a sidewall and the space defined by the bottom and the sidewall may be filled with a liquid. The shape of the bottom, which is not particularly limited, may be a polygon such as a triangle and a square or a circle (including a circle, a substantial circle, an ellipse and a substantial ellipse). The sidewall is formed so as to surround the outer periphery of the bottom. Usually, the opposite side to the bottom is opened. The shape of the opening is preferably identical with the shape of the bottom. The opening preferably has a circular shape having an opening width (for example, r in FIG. 2) of preferably 30 to 60 mm and particularly 35 mm. This is the same size as that of a petri dish routinely used in cell culture. For the reason that the vessel can be easily prepared from a general petri dish, and easily adapted to an existing culture apparatus and others, the vessel having the aforementioned size is preferable. Note that, the cell culture vessel may have a lid similarly to a general petri dish.

The wall surface of a recessed part forming a microwell preferably is an inclined plane standing up from the deepest portion to the outer periphery. As the inclined plane, e.g., a curved profile standing up from the lowest (deepest) position of a recessed part of a microwell to the outer periphery or a stepwise profile can be appropriately employed. In particular, it is preferable that the inclined plane has a linear portion, more specifically, the inclined plane wholly or partly has a portion linearly standing up from the lowest (deepest) position of a recessed part to the outer periphery. Owing to the presence of the linear portion, migration of a cell disposed in a microwell is suppressed and the cell can be easily fixed in the deepest portion of the microwell. With this mechanism, a clear image can be obtained when a cell is observed by a microscope. Such an inclined plane is preferably formed of a conical surface or a side surface of a truncated cone. In the case of a conical surface, the microwell is constituted such that the deepest portion of a microwell corresponds to the tip of the cone. In this case, the deepest portion of the microwell, in other words, the tip of a cone, may be rounded. In the case where the inclined plane is formed of the side of a truncated cone, a truncated cone is disposed in such a manner that the either surface having a narrower area of the upper or lower surfaces of the truncated cone corresponds to the deepest portion of the microwell.

The depth of a microwell, which means a value of the vertical depth measured from the opening of the microwell to the deepest portion, is preferably 0.05 to 0.5 mm. If a microwell is too shallow, a cell moves during e.g., transportation of a culture vessel and during cell division and may go out from the microwell. Because of the risk, the depth of a microwell is set so as to keep a cell within the microwell without fail. For example, in order to keep a cell within a microwell, it is preferable that the depth corresponds to ⅓ or more of the maximum diameter of the cell and further preferably ½ or more. In contrast, if a microwell is too deep, it is difficult to introduce culture medium and a cell into the microwell. Thus, the depth is appropriately set so as to keep a cell within a microwell and not to be extremely deep. For example, the upper limit of the depth value can be set three times or less of the opening width of the opening of a microwell. In order to easily introduce culture medium, the depth is preferably equal to or lower than of the opening width of a microwell and particularly preferably ½ or less.

If the surface roughness value of the wall surface of a microwell, in particular, the inclined plane, is large, when an image obtained by transmission observation by a microscope is subjected to a contour extraction process, a clear outline of the obtained image may not be obtained due to unevenness on the inclined plane. Because of this, it is preferable that the surface roughness value is as small as possible. More specifically, the maximum height Ry (when a reference-length in the direction of the average line is sampled from a roughness curve, the distance between the peak line and the valley bottom line in the sampled portion is referred to Ry) is preferably below 1.0 μm and particularly preferably below 0.5 μm. Note that, the degree of the surface roughness of the inclined plane can be reduced by enhancing processing accuracy of a mold by applying e.g., polishing processing, when the mold of a culture vessel is prepared.

A plurality of microwells are disposed on the bottom of a cell culture vessel and constitute a cell containing section. A plurality of cell containing sections each constituted of such a plurality of group of microwells may be disposed on the bottom and may not be disposed close to each other.

A cell containing section in which a plurality of microwells are disposed may be surrounded by an inner wall and partitioned from other portions of the culture vessel (for example, indicated by reference symbol 8 in FIG. 1 and FIG. 2). If a plurality of microwell groups are present at the bottom of a cell culture vessel, it is preferable that individual groups are each directly surrounded by an inner wall. Usually in culturing e.g., fertilized eggs, a droplet of culture medium containing fertilized eggs is formed in a culture vessel and covered with oil to prevent drying. If microwell groups formed in adjacent to each other are further surrounded by an inner wall, culture medium is contained therein to form a stable drop, thereby preventing dispersion of culture medium. For the same reason, culture medium is covered with oil such as a mineral oil.

The material of a cell culture vessel is not particularly limited. Specific examples thereof include inorganic materials such as metal, glass and silicon; and organic materials such as plastics (for example, a polystyrene resin, a polyethylene resin, a polypropylene resin, an ABS resin, nylon, an acrylic resin, a fluorine resin, a polycarbonate resin, a polyurethane resin, a methylpentene resin, a phenol resins, a melamine resin, an epoxy resin, and a vinyl chloride resin). The cell culture vessel can be produced by a method known to those skilled in the art. For example, a culture vessel is formed of a plastic material by a customary molding method, for example, injection molding.

The cell culture vessel is preferably subjected to a surface hydrophilic treatment such as a plasma treatment in order to prevent nonspecific adhesion of cultured cells and inhomogeneity of culture medium drop by surface tension. The number of bacteria (bioburden number) attached to a vessel manufactured is preferably 100 cfu/vessel or less. Furthermore, it is preferable that a sterilization treatment such as y sterilization is applied.

To the cell culture vessel, a surface treatment or surface coating which can facilitate growth of fertilized eggs may be applied. Particularly, when fertilized eggs are co-cultured with cells of other organs (for example, endometrial membrane cells or fallopian tube epithelial cells) in order to facilitate the growth of the fertilized eggs, these cells must be previously attached to a culture vessel. In such a case, it is advantageous that the surface of the culture vessel is coated with a cell-adhesive material.

Examples of a desired cell for culture include, but are not particularly limited to, a fertilized egg, an egg cell, an ES cell (embryonic stem cell) and iPS cell (induced pluripotent stem cell). The egg cell means an unfertilized egg cell, and includes an immature oocyte and a mature oocyte. The fertilized egg starts cleavage after fertilization, increases in cell number, like a 2-cell stage to a 4-cell stage and an 8-cell stage and develops into morula and blastocyst. Examples of the fertilized egg include the early embryos such as a 2-cell embryo, a 4-cell embryo and an 8 cell embryo, morula and blastocyst (including early blastocyst, expanded blastocyst and hatched blastocyst). The blastocyst means an embryo consisting of external cells having a potential of forming the placenta and inner cell mass having a potential of forming an embryo. The ES cell means an undifferentiated pluripotent or totipotent cell obtained from the inner cell mass of the blastocyst. The iPS cell means a somatic cell (principally, fibroblast) having pluripotency (like ES-cell), which is acquired by introducing several types of genes (transcription factor) into a somatic cell. More specifically, examples of the cell include a group of cells such as a fertilized egg and blastocyst.

The cell culture vessel of the present invention is suitable for culturing preferably mammalian cells and avian cells and particularly mammalian cells. The mammal means a warm-blooded vertebrate. Examples thereof include primates such as a human and a monkey; rodents such as a mouse, a rat and rabbit; pet animals such as a dog and a cat; and farm animals such as a cow, a horse and a pig. The cell culture vessel of the present invention is particularly suitable for culturing a human fertilized egg.

Figure 16:
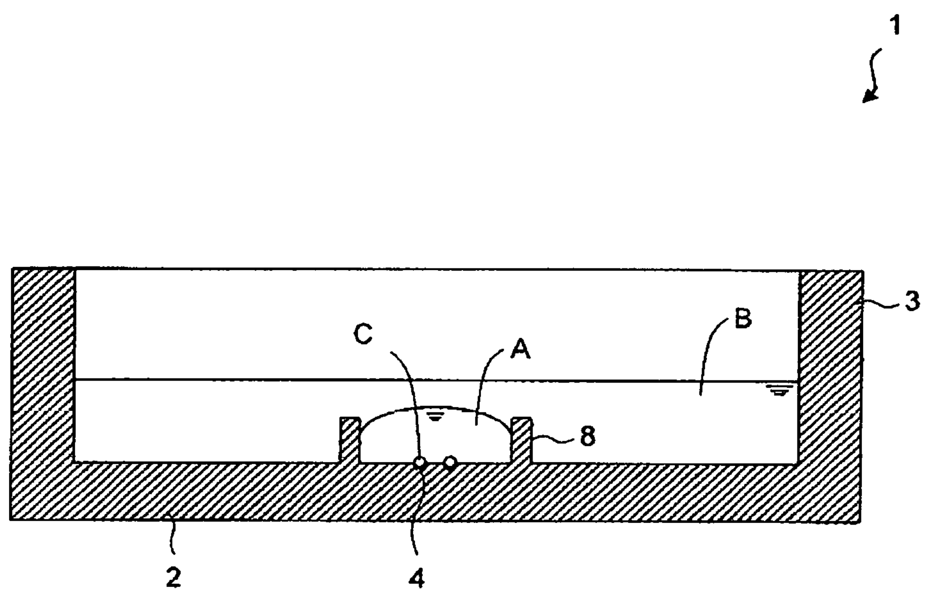
FIG. 16 is a schematic view showing a vertical cross-sectional view of an embodiment of a method for culturing cells using the cell culture vessel according to the present invention.

Usually, culture medium A is added so as to cover the microwell and oil B is added so as to cover the culture medium and then cell C is added to the culture medium. These operations are carried out usually by use of tools such as a pipette or a glass capillary. Since the cell culture vessel of the present invention has a large opening, these operations can be relatively easy carried out (FIG. 16).

Culture is usually performed by placing the cell culture vessel in an incubator which brings an ambient atmosphere containing a gas required for growth and maintenance of a cultured cell and constant ambient temperature. Examples of the requisite gas include water vapor, free oxygen ($0_2$) and carbon dioxide ($CO_2$). The pH of the culture medium can be stabilized within a certain period of time by controlling ambient temperature and $CO_2$ content. Stable pH can be obtained by stabilizing $CO_2$ content and temperature. The culture conditions such as temperature, gas and culture medium, can be controlled also by comparing the image of a cell during culture to a pre-stored image by use of an image comparison program.

For example, if a fertilized egg is cultured, usually whether the cultured fertilized egg is satisfactory and suitable or not for implantation into the uterus is determined. The determination may be automatically performed or manually by e.g., a microscope. In automatic determination of a cultured cell, the image of a cell in a culture vessel is captured by a microscope, photographed by a detection apparatus such as a CCD camera and subjected to a contour extraction process in which a portion corresponding to the cell is extracted from the image. The extracted cell image is analyzed by the image analysis apparatus to determine the quality of the cell. As the image contour extraction process, for example, a process described in JP Patent Publication (Kokai) No. 2006-337110 can be used.

When a microwell has a bottom surface parallel to the bottom of a cell culture vessel and side surface perpendicular to the bottom, a cell migrates within the microwell and sometimes comes in contact with the side surface. If a cell of this state is photographed, it is difficult to extract a cell image from a photographed image in a contour extraction process. However, if the wall surface of a microwell has an inclined plane, preferably has a cone-shaped or truncated cone-shaped portion, the cell to be cultured naturally stays at the bottom portion of the microwell. Thus, even if the microwell has a side surface in perpendicular to the bottom of the cell culture vessel at a site close to the opening than the inclined plane, the cell would not remain in contact with the perpendicular surface. The contour extraction process of the photo image of a cell can be carried out without a problem.

The specification incorporates the contents of the specifications and drawings described in JP Application Nos. 2013-188205 and 2014-027771 on which the priority of this application is based.

All publications, patents and patent applications cited in the specification are incorporated herein in their entireties by reference.

REFERENCE SIGNS LIST

1: Cell culture vessel
2: Sidewall
3: Bottom
4: Microwell
5: Cell containing section
6: Identifier
7: Second identifier
8: Inner wall
r: Opening width of cell culture vessel
R: Opening width of a microwell
a: Pitch of a microwell
A: Culture medium
B: Oil
C: Cell

The invention claimed is:

1. A cell culture vessel comprising a bottom and a sidewall, wherein the bottom has a cell containing section in which a plurality of microwells for containing cells are disposed, wherein the plurality of microwells comprises 4 or more microwells whose centroids are positioned on a same axis and includes every microwell present on the cell culture vessel, one or more microscopic identifiers are disposed in the vicinities of each of the 4 or more microwells and outside the 4 or more microwells so as to form respective identifier-microwell pairs, said microscopic identifiers being visible under a microscope and disposed on the same axis, and the relative position of each of the one or more microscopic identifiers to a partner microwell varies in every pair.

2. The cell culture vessel according to claim 1, wherein, in the top view, each of the microscopic identifiers has a smaller area than an opening of each of the microwells.

3. The cell culture vessel according to claim 1, wherein the microscopic identifiers have a dot or line shape.

4. The cell culture vessel according to claim 1, further comprising a second identifier for specifying orientation of the cell culture vessel, wherein, in the top view, the second identifier has a larger area than the opening of each of the microwells so as to be visually confirmed.

5. The cell culture vessel according to claim 1, wherein at least one of the 4 or more microwells is paired with a plurality of the microscopic identifiers.

6. The cell culture vessel according to claim 5, wherein the plurality of microscopic identifiers paired with the at least one microwell are different in shape.

7. The cell culture vessel according to claim 1, wherein the vicinity of the microwell is divided into a plurality of regions and the presence or absence of the microscopic identifier in the regions varies in every microwell-identifier pair.

8. The cell culture vessel according to claim 1, wherein a distance between each of the one or more microscopic identifiers and its partner microwell varies in every pair, the distance being defined as the distance between the centroid of the microwell and a centroid of the figure formed by each of the one or more microscopic identifiers, or an angle α of each of the one or more microscopic identifiers to its partner microwell varies in every pair, the angle α being defined as the angle formed between a straight line parallel to a straight line X drawn at the bottom of the cell culture vessel in a top view, and a straight line Y connecting the centroid of the microwell and the centroid of the figure formed by each of the one or more microscopic identifiers.

9. The cell culture vessel according to claim 1, wherein the one or more microscopic identifiers have a shape selected from the group consisting of a polygon, an arrow, a line, a dot, and bar codes.

10. A cell culture vessel comprising a bottom and a sidewall, wherein the bottom has a cell containing section in which a plurality of microwells for containing cells are disposed, wherein the plurality of microwells comprises 4 or more microwells and includes every microwell present on the cell culture vessel, one or more microscopic identifiers are disposed in the vicinities of each of the 4 or more microwells and outside the 4 or more microwells so as to form respective identifier-microwell pairs, said microscopic identifiers being visible under a microscope, the relative position of each of the one or more microscopic identifiers to a partner microwell varies in every pair, and all of the microscopic identifiers are disposed to right sides alone, left sides alone, upper sides alone or lower sides alone with respect to the centroid of each of the microwells.

11. The cell culture vessel according to claim 10, wherein, in the top view, each of the microscopic identifiers has a smaller area than an opening of each of the microwells.

12. The cell culture vessel according to claim 10, wherein the microscopic identifiers have a dot or line shape.

13. The cell culture vessel according to claim 10, further comprising a second identifier for specifying orientation of the cell culture vessel, wherein, in the top view, the second identifier has a larger area than the opening of each of the microwells so as to be visually confirmed.

14. The cell culture vessel according to claim 10, wherein at least one of the 4 or more microwells is paired with a plurality of the microscopic identifiers.

15. The cell culture vessel according to claim 14, wherein the plurality of microscopic identifiers paired with the at least one microwell are different in shape.

16. The cell culture vessel according to claim 10, wherein the vicinity of the microwell is divided into a plurality of regions and the presence or absence of the microscopic identifier in the regions varies in every microwell-identifier pair.

17. The cell culture vessel according to claim 10, wherein a distance between each of the one or more microscopic identifiers and its partner microwell varies in every pair, the distance being defined as the distance between the centroid of the microwell and a centroid of the figure formed by each of the one or more microscopic identifiers, or an angle α of each of the one or more microscopic identifiers to its partner microwell varies in every pair, the angle α being defined as the angle formed between a straight line parallel to a straight line X drawn at the bottom of the cell culture vessel in a top view, and a straight line Y connecting the centroid of the microwell and the centroid of the figure formed by each of the one or more microscopic identifiers.

18. The cell culture vessel according to claim 10, wherein the one or more microscopic identifiers have a shape selected from the group consisting of a polygon, an arrow, a line, a dot, and bar codes.

* * * * *